United States Patent
Pfeiffer et al.

(10) Patent No.: US 7,588,542 B2
(45) Date of Patent: Sep. 15, 2009

(54) DEVICE FOR DETERMINING A HEMODYNAMIC PARAMETER

(75) Inventors: Ulrich J. Pfeiffer, Munich (DE); Reinhold Knoll, Munich (DE); Stephan Regh, Munich (DE)

(73) Assignee: Pulsion Medical Systems AG, Munich (DE)

(*) Notice: Subject to any disclaimer, the term of this patent is extended or adjusted under 35 U.S.C. 154(b) by 604 days.

(21) Appl. No.: 11/130,355

(22) Filed: May 16, 2005

(65) Prior Publication Data
US 2005/0267379 A1 Dec. 1, 2005

(30) Foreign Application Priority Data
May 17, 2004 (DE) .................. 10 2004 024 334

(51) Int. Cl.
*A61B 5/02* (2006.01)
(52) U.S. Cl. ..................................... 600/485
(58) Field of Classification Search .................. 600/485
See application file for complete search history.

(56) References Cited

U.S. PATENT DOCUMENTS

| 4,821,735 | A | | 4/1989 | Goor et al. |
| 5,423,323 | A | * | 6/1995 | Orth ............................ 600/486 |
| 6,315,735 | B1 | | 11/2001 | Joeken et al. |
| 2002/0120204 | A1 | * | 8/2002 | Pfeiffer et al. ............... 600/505 |

FOREIGN PATENT DOCUMENTS

| DE | 198 14 371 | 10/1999 |
| DE | 699 05 240 | 11/2003 |
| EP | 1 236 435 | 9/2002 |
| EP | 1 062 596 | 2/2003 |
| JP | 62-231619 | 10/1987 |
| WO | WO99/02086 | 1/1999 |

OTHER PUBLICATIONS

Irlbeck, M. et al "Die kontinuierliche Messung des Herzzeitvolumens mit der Pulskonturanalyse" (Continuous measurement of cardiac output with pulse contour) *Anaesthesist* (1955); vol. 44, pp. 493-500; in German + English translation thereof.

* cited by examiner

*Primary Examiner*—Charles A Marmor, II
*Assistant Examiner*—Christian Y Jang
(74) *Attorney, Agent, or Firm*—Collard & Roe, P.C.

(57) ABSTRACT

An arterially measured pressure signal is continuously read in and temporarily stored in the working memory (RAM). The function p(t) is processed by the central processing unit (CPU), to calculate the heart/time volume PCCO and other hemodynamic parameters. The calculation comprises the following steps: The systemic vascular resistance $SVR_k$ is calculated for the current pulse period. The stroke volume $SV_k$ is numerically determined from the pressure values of a pulse period, according to the following equation:

$$SV_k \propto \sum \left( \frac{p_i(t)}{SVR_k} + C_k(p_i)\frac{dp_i}{dt} \right)$$

with the compliance $C(p)=(MAP-CVP)_k/[SVR \cdot <dp/dt>_k] \cdot f(p)$. The difference between the mean arterial pressure MAP and the central venous pressure CVP, and the mean incline of the pressure curve in the diastole <dp/dt>, are re-determined for the current pulse period. The heart/time volume calculated in the current pulse period results from $PCCO_k=SV_k \cdot HR$. Therefore, continuous recalibration of the systemic vascular resistance and of the compliance takes place, from the continuously determined pressure measurement data.

29 Claims, 1 Drawing Sheet

DEVICE FOR DETERMINING A HEMODYNAMIC PARAMETER

BACKGROUND OF THE INVENTION

1. Field of the Invention

The present invention relates to a device for determining a hemodynamic parameter of a patient by means of pulse contour analysis.

2. The Prior Art

The determination of hemodynamic parameters, particularly the heart/time volume (cardiac output CO), by means of pulse contour analysis on the basis of a non-linear air dome model, has been described in detail in German Patent No. DE 198 14 371 A1 as well as in the literature listed there, which goes even further. The fundamental measurement variable for pulse contour analysis is a pressure that approximately corresponds to the aorta pressure, which is continuously measured, for example, by means of an arterial catheter in a leg artery. A pulse contour analysis system from Pulsion Medical Systems AG is commercially available under the designation PiCCO.

Significant variables in the determination of hemodynamic parameters, proceeding from the function P(t), i.e. the time progression of the pressure signal that approximately corresponds to the aorta pressure, are, in particular, the systemic vascular resistance (SVR), as well as furthermore the so-called compliance (C). The former is explained and understood as the flow-through resistance of the vascular system of the large blood circulation system, the latter as the resilience in the region of the aorta. In a substitute schematic, these variables can be represented as resistance and capacitance. In the case of older approaches, in particular, the compliance is sometimes ignored.

A device and a method for determining the compliance are disclosed in DE 198 14 371 A1.

In the case of conventional implementations of pulse contour analysis, calibration values that are determined within the scope of a calibration measurement and not changed after that are included in the determination of the systemic vascular resistance and the compliance (unless the latter is ignored). This calibration measurement includes the determination of a calibration value of the heart/time volume by trans-pulmonary thermo-dilution measurement.

For the heart/time volume determined by pulse contour analysis (pulse contour cardiac output, PCCO), which is calculated as the product of pulse frequency (heart rate, HR) and stroke volume (SV), the following equations are used.

The stroke volume (SV) is calculated by integration over a pulse period, or over the systole, according to the equation $$SV \propto \int \left( \frac{p(t)}{SVR} + C(p) \cdot \frac{dp}{dt} \right) dt$$

(with time t, pressure p, systemic vascular resistance SVR, compliance C).

In this connection, k is evaluated by numerical integration for every pulse period k, whereby the compliance is inserted in the form $$C(p) = \frac{CO_{TD}}{\left( \frac{dp}{dt} \right)_{Cal}} \cdot \frac{1}{\frac{3}{MAP_{Cal}} p - 3 - \frac{1}{MAP_{Cal}^2} p^2}$$

(with $CO_{TD}$:=calibration value of the heart/time volume determined by means of trans-pulmonary thermo-dilution measurement, $<dp/dt>_{Cal}$:=mean [negative] incline of the pressure curve in the diastole during the calibration measurement, $P_d$:=diastolic pressure; $MAP_{Cal}$:=mean arterial pressure during the calibration measurement).

The parameters $CO_{TD}$, $MAP_{Cal}$ and $<dp/dt>_{Cal}$ are only determined within the scope of the calibration measurement and then used for all the heart/time volume calculations.

For the systemic vascular resistance SVR, as well, a calibration value determined in accordance with the equation $$SVR_{Cal}=(MAP-CVP)_{Cal}/CO_{TD}$$

is used (with MAP:=mean arterial pressure, CVP:=central venous pressure), which value is determined within the scope of the calibration measurement and then used as a constant for all the heart/time volume calculations.

It has been shown that the hemodynamic parameters determined by pulse contour analysis sometimes decrease in quality, as the duration of patient monitoring increases (calculated starting with the calculation measurement). In other words, the likelihood that the hemodynamic parameter obtained by pulse contour analysis will deviate from the actual physiological conditions by more than a certain predetermined measure increases.

In order to counteract this, the calibration measurement by thermo-dilution can be repeated at shorter intervals. However, this is connected with some effort and expenditure, particularly with the administration of a bolus injection, and this means additional stress for the patient being monitored, as well as putting a time burden on the personnel involved, thereby reducing the availability of that personnel for other tasks.

SUMMARY OF THE INVENTION

It is therefore an object of the invention to provide a device for determining hemodynamic parameters by means of pulse contour analysis, in the use of which a regular repetition of a calibration measurement by thermo-dilution is not necessary, and which nevertheless yields a measurement data evaluation of unchanging quality.

This object is accomplished with a device for determining a hemodynamic parameter of a patient by means of pulse contour analysis, in accordance with claim 1.

Therefore, continuous recalibration of the systemic vascular resistance, preferably also of the compliance, takes place by means of the parameters obtained from the continuously determined pressure measurement data.

According to the invention, the determination of the heart/time volume by pulse contour analysis PCCO can take place, in its fundamental traits, as described above. However, one or more of the parameters that would conventionally be determined within the scope of the calibration measurement and then treated as a constant are regularly recalculated from the function p(t), preferably once for every pulse period.

For this purpose, a continuous recalculation takes place at first for the systemic vascular resistance SVR. Fundamentally, the value SVR can be derived from the equation $$SVR=(MAP-CVP)/CO.$$

However, simply inserting the heart/time volume PCCO obtained by pulse contour analysis for the heart/time volume CO results in a circular equation. This can be solved by an iteration process, but this can result in instabilities in the case of drastic changes in the systemic vascular resistance SVR. Therefore, it is advantageous to implement additional or alternative criteria for a change in the systemic vascular resistance SVR.

Suitable parameters that can be used to take into consideration changes in the systemic vascular resistance SVR are, in particular:
the systolic pressure $P_s$,
the mean arterial pressure MAP,
the pulse pressure $PP=(P_s-P_d)$,
the difference of the pressure at the transition between systole and diastole and the diastolic pressure $(P_n-P_d)$,
the mean incline of the pressure curve in the diastole <dp/dt>.

The diastolic phase of the pulse period can advantageously be approximated by means of exponential drop:

$$p(t)-\text{offset}=\text{const.}\cdot\exp(-t/\tau)$$

whereby offset refers to the abscissa value at the beginning of the exponential drop, $\exp(-t/\tau)$ is an exponential function with the argument $(-t/\tau)$, and the time, constant $\tau$ can be obtained from the pressure curve according to the following equation:

$$\tau=[p(t)-\text{offset}]/(dp/dt)$$

For the simplified substitute schematic of a parallel circuit of capacitance (compliance) and resistance (systemic vascular resistance), the following applies:

$$\tau=SVR\cdot C(p).$$

Even if these equations are fundamentally sufficient, the results can be improved by using empirical equations as a function of the above parameters, particularly by means of the following equation $$SVR=SVR_{cal}(\tau/\tau_{cal})^a\cdot(Pd/Pd_{cal})^b$$

which is preferably applied, where $SVR_{cal}$ is a calibration value of the systemic resistance, $\tau_{cal}$ is a calibration value of the time constant $\tau$, Pd is the diastolic arterial pressure, $Pd_{cal}$ is a calibration value of the diastolic arterial pressure, and a, b are empirically determined or estimated exponents. The calibration values $SVR_{cal}$, $\tau_{cal}$, and $Pd_{cal}$ can be determined within the scope of a calibration measurement including thermo-dilution measurement. The parameter selection a=0.3 and b=1 results in a good adaptation, but under some circumstances, a better adaptation can be achieved by means of a slight change in these parameters.

The (arterial) diastolic pressure Pd and the pressure at the transition between systole and diastole Pn are preferably re-determined regularly, to the extent that they are needed for the further calculation of hemodynamic parameters. It is particularly advantageous in this connection to implement improved paths for determining the transition between systole and diastole, the so-called iachrotic notch, as well as for determining the diastolic pressure.

The first ($y=dP/dt$) and the second ($y=d^2p/dt^2$) derivation of the function p(t) are determined using suitable smoothing algorithms. From them, an indication function is calculated, which represents a measure of the local curvature of the function p(t). The curvature function $$K=\dot{y}(1+y)^{3/2}$$

is particularly suitable. It can be interpreted as the reciprocal value of a local curvature radius. Preferably, an axis adjustment is provided for the function p(t), in such a manner that a typical progression of an arterial pressure function at the transition between systole and diastole, obtained from empirically collected data, possesses approximately the shape of an arc.

The position of the maximum of the curvature function K is determined within the range of the function p(t), in which this function assumes values from 90% to 10%, preferably 75% to 10% of its maximal value within the current pulse period. The corresponding point in time is corrected, if necessary, taking into consideration delay elements in the measurement set-up, for example filters. If the maximum of the curvature function K (after this correction, if applicable), lies within 70% of the duration of the current pulse period (or the duration of the prior pulse period, if the calculation is carried out in real time, before the end of the current pulse period), then the location of the maximum of the curvature function K (corrected, if applicable) is interpreted as the point in time of the transition between systole and diastole. Otherwise, the transition between systole and diastole is established at 70% of the duration of the current pulse period (or the duration of a prior pulse period, if the calculation is performed in real time, before the end of the current pulse period). Optionally, an additional plausibility check can also be provided, taking into consideration pulse duration, ejection time, etc.

Alternatively, it is possible to do without the determination of the curvature function, and instead of the maximum of the curvature function K, the maximum of the second derivation y of the function p(t), if necessary after a corresponding correction, can be interpreted as the point in time of the transition between systole and diastole.

As mentioned above, in the determination of the stroke volume, integration frequently takes place only by way of pressure values of the systole. Also, in order to increase the accuracy of the stroke volume determination, the above, improved determination of the transition between systole and diastole is therefore preferably provided.

In the determination of the diastolic pressure Pd, the following approach has proven to be particularly advantageous, which takes into consideration the influence of the limited measurement frequency, i.e. the frequency at which the pressure measurement system that determines the arterial pressure responds (and accordingly functions as a low-pass filter).

Proceeding from the lowest pressure measured, a linear regression of a suitable length is undertaken. It is advantageous to assume approximately 100 milliseconds or twice the reciprocal value of the measurement frequency as a suitable length. If the length of the diastole is shorter than twice this length, the lowest pressure measured is assumed to be the diastolic pressure Pd. Otherwise, the beginning of the regression is displaced by a suitable length, preferably half the length of the regression, in the direction of the systolic peak, and extrapolated in the opposite direction. The intersection point of the extrapolation with the extrapolated linear regression of the pressure curve in the region of its maximal incline then gives the diastolic pressure. Preferably, only data points within 20% to 80% of the pulse amplitude (highest pressure measured minus lowest pressure measured during the pulse period) are taken into consideration for determining the range of maximal incline.

In the calculation formula for the compliance indicated initially, the value $CO_{TD}$ can be replaced with the term $$(MAP-CVP)/SVR$$

whereby the difference between the mean arterial pressure MAP and the central venous pressure CVP is regularly re-determined. In this connection, either the values of the current or of the prior pulse period can be used, or averaged values over several (for example between 10 and 50) prior pulse periods, or several (for example approximately 30) seconds. The mean incline of the pressure curve in the diastole <dp/dt> is also preferably regularly re-determined.

Preferably, a correction function having the form $$f(p)=1/[k_1 \cdot p/MAP - k_2 - k_3 \cdot (p/MAP)^2]$$

with empirically determined or estimated coefficients $k_1$, $k_2$, $k_3$, leads to better results in determining the compliance. The section of the coefficients $k_1=9/5$, $k_2=17/25$, and $k_3=9/2$ leads to a suitable adaptation. In addition, other suitable adaptations can exist.

For the compliance, it is therefore true that $$C(p) = (MAP - CVP)/(SVR \cdot <dp/dt>) \cdot f(MAP,p)$$

with $$f(MAP,p) = 1/[1.8 \cdot p/MAP - 0.68 - 4.5 \cdot (p/MAP)^2]$$

whereby the parameters MAP, SVR, and <dp/dt>, if necessary also CVP, are regularly re-determined.

However, embodiments in which the parameters of the compliance function are not regularly recalculated, or the compliance is ignored, are also in-accordance with the invention.

BRIEF DESCRIPTION OF THE DRAWINGS

Other objects and features of the present invention will become apparent from the following detailed description considered in connection with the accompanying drawing. It is to be understood, however, that the drawing is designed as an illustration only and not as a definition of the limits of the invention.

DETAILED DESCRIPTION OF THE PREFERRED EMBODIMENT

Figure 1:
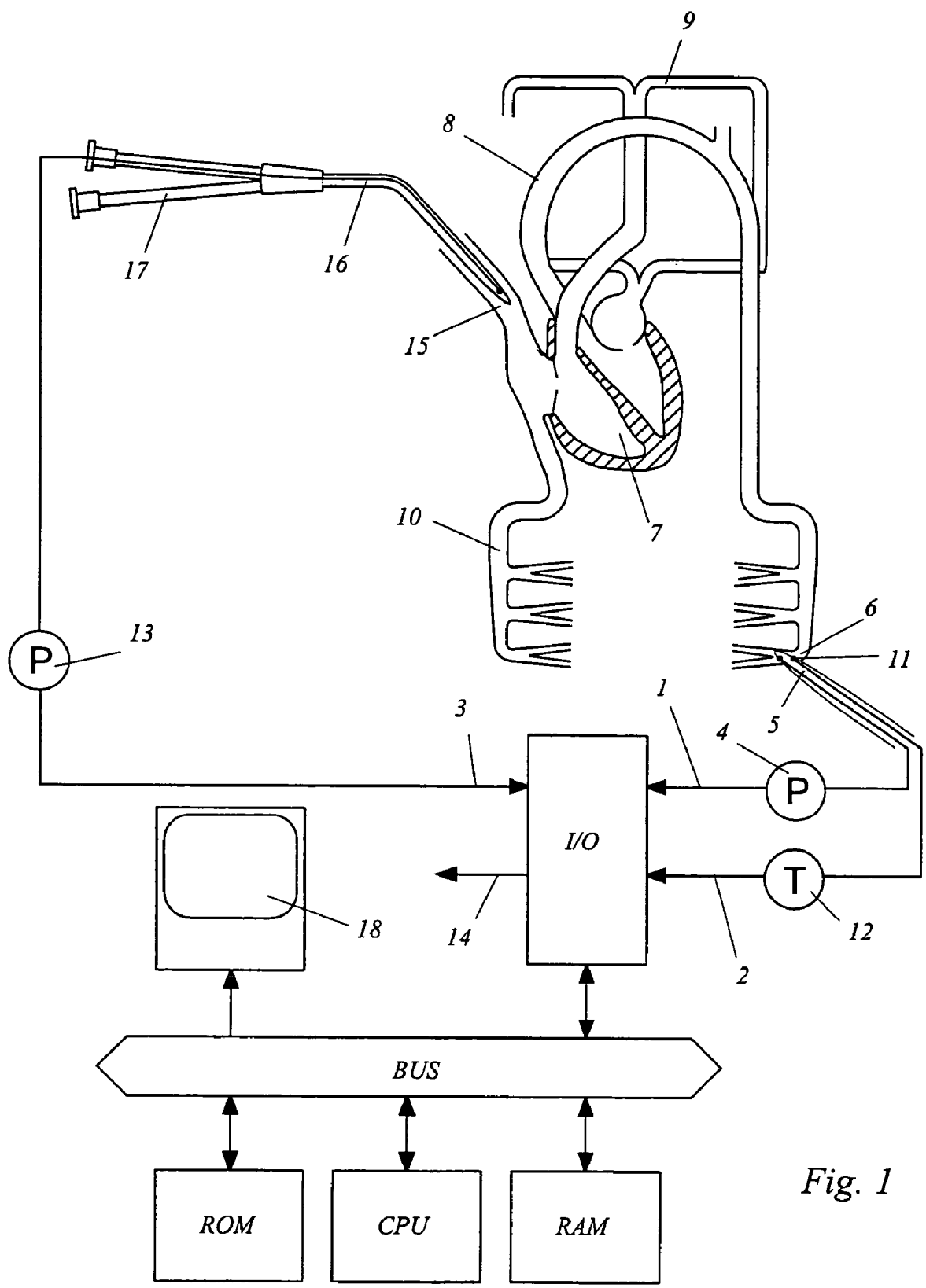
FIG. 1 shows a greatly simplified block schematic of a device according to the invention, as well as a segment of the vascular system of a patient, shown merely in outline.

The device from FIG. 1 has an input/output sub-system (I/O) with three input channels 1, 2, 3.

A pressure signal that corresponds at least approximately to the aorta pressure of the patient is continuously read in by way of the first input channel 1. This can be an analog sensor signal, which is digitalized by means of an analog/digital converter, or a digital signal is already read in from an external pressure measurement transformer 4.

In practice, an arterial pressure that is measured, preferably as close to the aorta as possible, by way of an arterial catheter 5, serves as a pressure that approximately corresponds to the aorta pressure. A leg artery 6 can serve as the measurement site, as is indicated in the outlined segment of the vascular system with heart 7, aorta arch 8, pulmonary circulatory system 9, and body circulatory system 10.

The arterial catheter 5 furthermore contains a temperature sensor 11, which can be used for a thermo-dilution measurement for calibration. The digital measurement signal of the related temperature measurement transformer 12 is read in by way of the second input channel 2. The temperature signal can also be read in as an analog signal and digitalized by means of an analog/digital converter.

A pressure signal that at least approximately corresponds to the central venous pressure CVP of the patient is read in by way of the third input channel 3. This signal, too, can be read in as an analog or digital signal, by way of another pressure measurement transformer 13. A suitable measurement site is the upper vena cava 15 of the patient. Alternatively, however, the central venous pressure CVP of the patient can also be estimated; under some circumstances, an estimation as a constant value is sufficient in this connection.

The central venous catheter 16 that is inserted has another lumen 17, by way of which a cooled bolus can be injected in order to carry out the trans-pulmonary thermo-dilution measurement. The calibration values $SVR_{cal}$, $\tau_{cal}$, and $Pd_{cal}$, for the systemic resistance, the time constant, and the diastolic arterial pressure, are determined within the scope of the calibration, as explained above.

An input/output sub-system (I/O) can have one or more output or control channels 14, which serve for the interaction with peripherals or the like, for example.

The components of the device that serve for signal processing are connected with one another by way of a central bus (BUS).

The pressure signal that is read in is temporarily stored in the working memory (RAM) as a function of time p(t). The function p(t) is processed by the central processing unit (CPU), in order to calculate the heart/time volume PCCO and other hemodynamic parameters from it. A corresponding control program, which causes the processing unit (CPU) to perform the corresponding calculation steps, is contained in the fixed memory (ROM).

In this connection, the processing comprises the following steps:

The transition between systole and diastole is determined as the site of the maximal curvature of the pressure curve, as described above.

The time constant $\tau$ is determined from the pressure curve, and the systemic vascular resistance $SVR_k$ is calculated for the current, $k^{th}$ pulse period, according to the equation $$SVR_k = SVR_{cal} \cdot (\tau/\tau_{cal})^a \cdot (Pd/Pd_{cal})^b.$$

The stroke volume $SV_k$ of the current pulse period is determined numerically from the pressure values of a pulse period, i.e. the pressure values of the systole of a pulse period, according to the following equation (with counting variable I):

$$SV_k \propto \sum \left( \frac{p_i(t)}{SVR_k} + C_k(p_i)\frac{dp_i}{dt} \right) \text{ where}$$

$$C(p) = (MAP - CVP)_k \Big/ \left[ SVR \cdot \left\{ \frac{dp}{dt} \right\}_k \right] \cdot f(p)$$

is inserted. The difference between the mean arterial pressure MAP and the central venous pressure CVP as well as the mean incline of the pressure curve in the diastole <dp/dt> are re-determined for the current pulse period. The correction function $f(MAP, pi)$ is calculated as described above.

The heart/time volume calculated in the current ($k^{th}$) pulse period is then obtained as $$PCCO_k = SV_k \cdot HR$$

The control program in the fixed memory (ROM) can, of course, contain additional routines that impart additional functionalities to the device.

The function p(t) can be displayed by way of a display sub-system 18, and the heart/time volume PCCO as well as other hemodynamic parameters can be output.

Of course, the device can be equipped with other components actually known to a person skilled in the art, for example mass memory media for recording raw data and/or calculated hemodynamic parameters. The processing unit (CPU) can be equipped with one or more conventional microprocessors, if necessary supported with co-processors for speeding up floating decimal operations, but also with so-called digital signal processors (DSP). Corresponding solutions, as well as other details of the hardware implementation, can be implemented analogous to usual pulse contour analysis devices according to the state of the art.

Accordingly, while only a few embodiments of the present invention have been shown and described, it is obvious that many changes and modifications may be made thereunto without departing from the spirit and scope of the invention.

What is claimed is:

1. A device for determining a hemodynamic parameter of a patient by pulse contour analysis, comprising:
    an input channel for reading in a pressure signal that changes over time and at least approximately corresponds to an aorta pressure of a patient, or an arterial pressure close to the aorta, as a function of time p(t); and
    an evaluation unit for calculating the hemodynamic parameter, using the function p(t) and a systemic vascular resistance of the body of the patient SVR,
    wherein the evaluation unit is adapted to regularly recalculate the systemic vascular resistance of the body of the patient SVR, using the function p(t) without requiring recalibration by thermodilution methods between repeated recalculations of the systemic vascular resistance, wherein the recalculation of the systemic vascular resistance SVR comprises a determination of a time constant $\tau$ of an approximately exponential pressure drop during a diastole.

2. A device according to claim 1, further comprising memory means (RAM) for temporarily storing the pressure signal read in, at least over a pulse cycle, as a function of time P(t).

3. A device according to claim 1, wherein the recalculation of the systemic vascular resistance is provided as the product $$SVR_{cal} \cdot (\tau/\tau_{cal})^a \cdot (Pd/Pd_{cal})^b$$

wherein $SVR_{cal}$ is a calibration value of the systemic vascular resistance,
$\tau_{cal}$ is a calibration value of the time constant $\tau$,
Pd is the diastolic arterial pressure,
$Pd_{cal}$ is a calibration value of the diastolic arterial pressure, and
a, b are empirically determined or estimated exponents.

4. A device according to claim 3, wherein $0.15 < a < 0.6$.

5. A device according to claim 3, wherein $0.5 < b < 2$.

6. A device according to claim 1, wherein the recalculation of the systemic vascular resistance SVR, takes into consideration a prior calculation of the systemic vascular resistance, and is provided according to the formula having the form $$SVR_k = SVR_{k-1} \cdot f$$

wherein $SVR_k$ is the recalculated systemic vascular resistance, $SVR_{k-1}$ is the systemic vascular resistance from the prior calculation, and $f$ is a correction function.

7. A device according to claim 1, wherein the evaluation unit is adapted to regularly recalculate parameters of a compliance function C(p), using the function p(t).

8. A device according to claim 7, wherein the recalculation of the compliance function C(p) is provided according to the formula $$C(p) = (MAP - CVP)_{k/[SVR \cdot <dp/dt>_k]} \cdot f(p)$$

wherein
$(MAP-CVP)_k$ is a difference between a mean arterial pressure and central venous pressure of the diastole of a current pulse period,
$<dp/dt>_k$ is a mean incline of an arterial pressure curve in the diastole of the current pulse period, and
$f(p)$ is a correction function.

9. A device according to claim 8, wherein the correction function possesses the form $$f(p) = 1/[k_1 \cdot p/MAP - k_2 - k_3 \cdot (p/MAP)^2]$$

with empirically determined or estimated coefficients $k_1$, $k_2$, $k_3$.

10. A device according to claim 9, wherein $k_1 = 9/5$, $k_2 = 17/25$, and $k_3 = 9/2$.

11. A device according to claim 1, wherein the hemodynamic parameter is a heart/time volume CO as a product of pulse rate HR and stroke volume SV.

12. A device according to claim 11, wherein the stroke volume is calculated as the integral $$\int \{p(t)/SVR + C(p) \cdot dp/dt\} dt$$

wherein SVR is the systemic vascular resistance.

13. A device according to claim 1, wherein the evaluation unit has differentiation means for forming a second derivation y" from the function p(t), as well as evaluation means for determining a site of maximal curvature of the function p(t), in a determination range between a maximal and a minimal function value of the pulse cycle, as a site of a transition between systole and diastole.

14. A device according to claim 1, further comprising output means for outputting the hemodynamic parameter.

15. A device according to claim 1, further comprising a connector for connecting an arterial catheter for the pressure measurement.

16. A device according to claim 1, further comprising an input channel for reading in a pressure signal that changes over time and at least approximately corresponds to a central venous pressure of the patient.

17. A device according to claim 16, further comprising a connector for connecting a central venous catheter for the pressure measurement.

18. A method for determining a hemodynamic parameter of a patient by means of pulse contour analysis, comprising the steps of:
    reading in a pressure signal that changes over time and at least approximately corresponds to an aorta pressure of a patient, or an arterial pressure close to the aorta, as a function of time p(t), and
    calculating the hemodynamic parameter, using a function p(t) and a systemic vascular resistance of the body of the patient SVR,
    wherein the systemic vascular resistance of the body of the patient SVR, is regularly re-calculated using the function p(t) without requiring recalibration by thermodilution methods between repeated recalculations of the systemic vascular resistance; and wherein the recalculation of the systemic vascular resistance SVR includes a determination of a time constant $\tau$ of an approximately exponential pressure drop during a diastole.

19. The method according to claim 18, wherein the recalculation of the systemic vascular resistance is provided as the product $$SVR_{cal} \cdot (\tau/\tau_{cal})^a \cdot (Pd/Pd_{cal})^b$$

wherein
$SVR_{cal}$ is a calibration value of systemic resistance,
$\tau_{cal}$ is a calibration value of the time constant $\tau$,
Pd is the diastolic arterial pressure,
$Pd_{cal}$ is a calibration value of diastolic arterial pressure, and
a, b are empirically determined or estimated exponents.

20. The method according to claim 19, wherein $0.15 < a < 0.6$.

21. The method according to claim 19, wherein $0.5 < b < 2$.

22. The method according to claim 18, wherein the recalculation of the systemic vascular resistance SVR takes into consideration a prior calculation of the systemic vascular resistance and is provided according to the formula having the form $$SVR_k = SVR_{k-1} \cdot f$$

wherein
$SVR_k$ is the recalculated systemic vascular resistance,
$SVR_{k-1}$ is the systemic vascular resistance from the prior calculation, and
$f$ is a correction function.

23. The method according to claim 18, wherein parameters of the compliance function C(p) are regularly recalculated, using the function p(t).

24. The method according to claim 23, wherein the recalculation of the compliance function C(p) is provided according to the formula $$C(p) = (MAP - CVP)_k / [SVR \cdot <dp/dt>_k] \cdot f(p)$$

wherein
$(MAP-CVP)_k$ is a difference between mean arterial pressure and central venous pressure of the diastole of a current pulse period,
$<dp/dt>_k$ is a mean incline of an arterial pressure curve in the diastole of the current pulse period, and
$f(p)$ is a correction function.

25. The method according to claim 24, wherein the correction function possesses the form $$f(p) = 1/[k_1 \cdot p/MAP - k_2 - k_3 \cdot (p/MAP)^2]$$

with empirically determined or estimated coefficients $k_1$, $k_2$, $k_3$.

26. The method according to claim 25, wherein $k_1 = 9/5$, $k_2 = 17/25$, and $k_3 = 9/2$.

27. The method according to claim 18, wherein the hemodynamic parameter is a heart/time volume CO as a product of the pulse rate HR and the stroke volume SV.

28. The method according to claim 27, wherein the calculation of the stroke volume is provided as the integral $$\int \{p(t)/SVR + C(p) \cdot dp/dt\} dt$$

wherein SVR is the systemic vascular resistance.

29. The method according to claim 18, wherein a second derivation y" from the function p(t) is formed, and a site of maximal curvature of the function p(t) is determined in a determination range between a maximal and a minimal function value of the pulse cycle, as a site of a transition between systole and diastole.

* * * * *

UNITED STATES PATENT AND TRADEMARK OFFICE
CERTIFICATE OF CORRECTION

PATENT NO. : 7,588,542 B2
APPLICATION NO. : 11/130355
DATED : September 15, 2009
INVENTOR(S) : Pfeiffer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1091 days.

Signed and Sealed this

Twenty-first Day of September, 2010

David J. Kappos
*Director of the United States Patent and Trademark Office*